United States Patent [19]
Shinohara et al.

[11] Patent Number: 5,998,611
[45] Date of Patent: Dec. 7, 1999

[54] PROCESS FOR PRODUCING CEPHEM COMPOUNDS IN AN AQUEOUS MEDIUM

[75] Inventors: Homare Shinohara, Ibaraki Prefecture; Masato Kodama; Kimio Hamamura, both of Chiba Prefecture; Hirofumi Kuroda, Ibaraki Prefecture, all of Japan

[73] Assignee: Eisai Chemical Co., Ltd., Ibaraki Prefecture, Japan

[21] Appl. No.: 08/936,839

[22] Filed: Sep. 25, 1997

[30] Foreign Application Priority Data

Sep. 25, 1996 [JP] Japan .................................. 8-253513

[51] Int. Cl.⁶ .................... C07D 501/46; C07D 501/44; C07D 501/20; C07D 501/24
[52] U.S. Cl. .................... 540/222; 540/215; 540/226; 540/227; 540/228; 540/230
[58] Field of Search .................................. 540/222, 226, 540/227, 228, 215, 230

[56] References Cited

U.S. PATENT DOCUMENTS 4,316,019  2/1982  Takaya ...................................... 544/28

FOREIGN PATENT DOCUMENTS 333154  3/1989  European Pat. Off. .

OTHER PUBLICATIONS

Barett, J. Antibiotics 50, pp. 100–102, 1997.

*Primary Examiner*—Mark L. Berch
*Attorney, Agent, or Firm*—Wenderoth, Lind & Ponnack, L.L.P.

[57] ABSTRACT

An industrially excellent, novel process for producing cephem compounds which are useful as medicines, particularly, antibiotics and represented by the following formula (III):

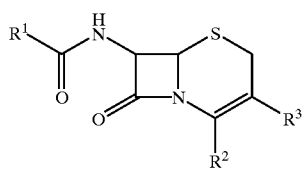

(III)

wherein $R^1$ means either group represented by the following formula:

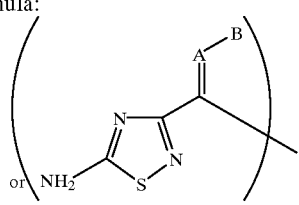

-continued

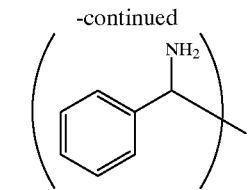

$R^2$ denotes a carboxyl group or a carboxyl anion, and $R^3$ stands for a lower alkyl group, a halogen atom, a lower alkyl group substituted by an aliphatic acyloxy group having 1–6 carbon atoms, or any one of the groups represented by the following formulae:

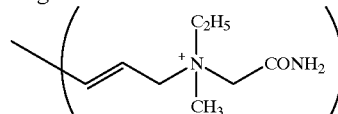

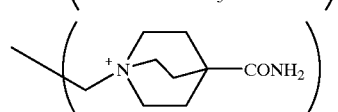

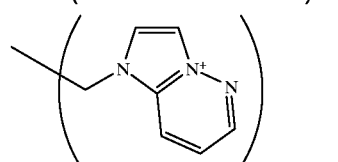

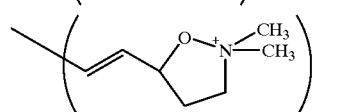

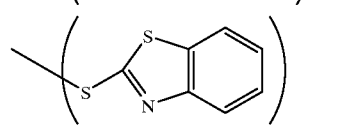

and

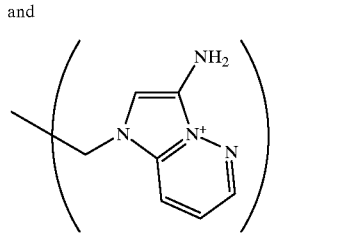

which comprises reacting in water a 3-cephem-4-carboxylate represented by the following formula (I):

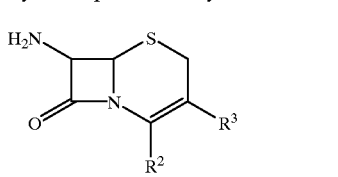

(I)

or a salt thereof with an acid chloride represented by the formula (II), $R^1COCl$.

10 Claims, No Drawings

PROCESS FOR PRODUCING CEPHEM COMPOUNDS IN AN AQUEOUS MEDIUM

FIELD OF THE INVENTION

The present invention relates to an industrially excellent, novel process for producing cephem compounds useful as medicines, particularly, antibiotics.

BACKGROUND OF THE INVENTION

Cephem compounds have heretofore been produced by reacting a 7-amino-3-cephem-4-carboxylate derivative or 7-aminocephalosporanic acid derivative, or the like with a carboxylic acid chloride or carboxylic acid in an organic solvent, thereby conducting an amidation.

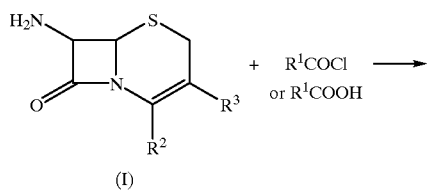

(I)

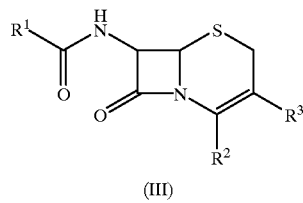

(III)

For example, Japanese Patent Application Laid-Open Nos.125,190/1977, 68,795/1978 and 68,796/1978, which correspond to GB 1576625 and GB 1576626, disclose reaction examples in which 2-methoxyimino-2-(2-amino-1,3-thiazol-4-yl)acetic acid is condensed with 7-amino-cepharosporanic acid in the presence of phosphorus oxychloride to produce ceftizoxime.

However, many of 7-amino-3-cephem-4-carboxylate derivatives are hardly soluble in organic solvents and require a large amount of a solvent upon their reactions. Therefore, their use has been extremely disadvantageous from the viewpoint of production cost. Besides, since organic solvents generally have toxicity or flammability, full measures must also be taken for equipment and the like from the viewpoint of work environment. As described above, the conventional production processes making use of an organic solvent have involved problems of bulk material cost and manufacturing facilities.

In addition, since the cephem compounds are used as medicines, products having extremely high purity are required. For this reason, the products are finally purified by column chromatography. Since the cephem compounds themselves are high-polar substances, reverse phase chromatography is in use for purification from the viewpoint of purification efficiency.

When the reaction is carried out using an organic solvent, however, it has been necessary to remove a large amount of the reaction solvent by concentration to replace it by a solvent (polar solvent) for chromatography. There has also been a problem that when the amount of the residual solvent is large due to insufficient concentration, purification efficiency of chromatography is lowered.

SUMMARY OF THE INVENTION

The present inventors have carried out an extensive investigation with a view toward solving the above-described problems. As a result, it has been found that water, which has high solubility to 7-amino-3-cephem-4-carboxylate derivatives, is cheap and involves no problem from the viewpoint of safety, is suitably used as a solvent for reactions of such derivatives, thus leading to completion of the present invention.

According to the present invention, there is thus provided a process for producing a cephem compound represented by the following formula (III):

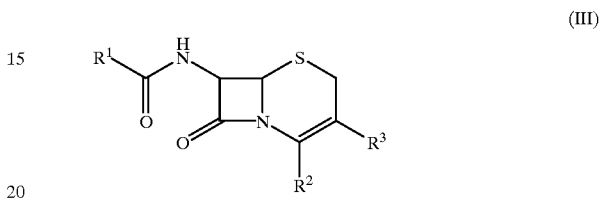

wherein $R^1$ means either group represented by the following formula:

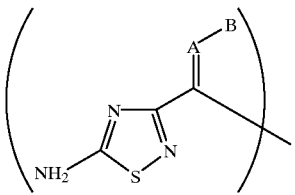

or

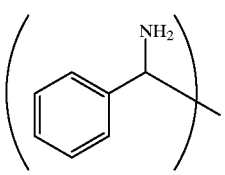

in which A denotes a nitrogen atom or a methine group, and B is a group selected from among lower alkoxy groups, halogenated lower alkoxy groups, a triphenylmethoxy group, lower alkyl groups, lower acyloxy groups and groups represented by the formula —$C(CH_3)_2COOR$ in which R means a hydrogen atom, an alkali metal atom, an alkaline earth metal atom or an organic cation, with the proviso that A and B may be either a geometric isomer (E) or (Z), $R^2$ denotes a carboxyl group or a carboxyl anion, and $R^3$ stands for a lower alkyl group, a halogen atom, a lower acyloxyalkyl group or any one of groups represented by the following formulae:

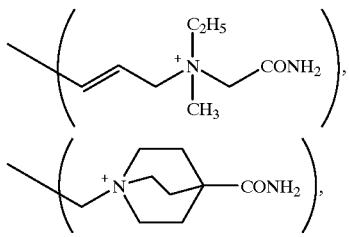

-continued

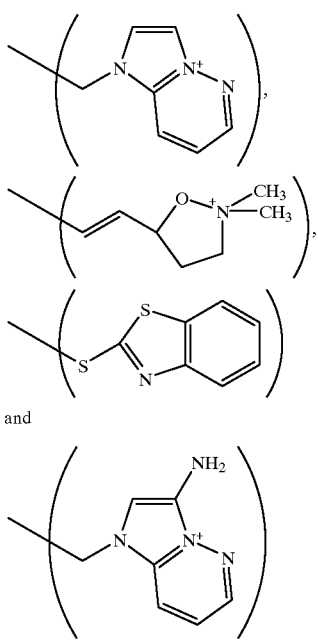

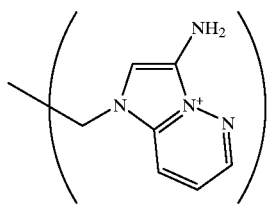

and

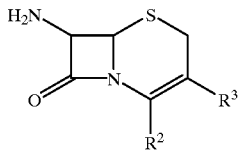

which comprises reacting in water a 3-cephem-4-carboxylate represented by the following formula (I):

(I)

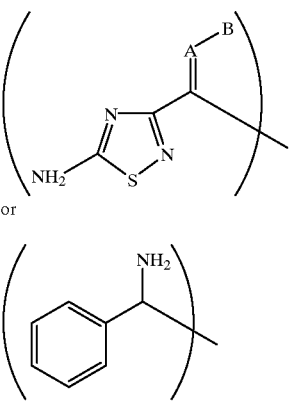

wherein $R^2$ and $R^3$ have the same meanings as defined above, or a salt thereof with an acid chloride represented by the formula (II);

$R^1COCl$ wherein $R^1$ has the same meaning as defined above.

The present invention has the advantage that the reaction mixture per se can be charged without replacing water by any other solvent, in a subsequent purification step by chromatography, and so the process is an industrially far more excellent production process of cephem compounds than the conventional process.

DETAILED DESCRIPTION OF THE PREFERRED EMBODIMENTS

The process according to the present invention for producing cephem compounds will hereinafter be described in detail.

First, the cephem compounds to be produced according to the present invention are represented by the following formula (III):

(III)

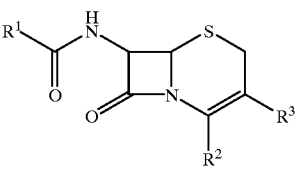

wherein $R^1$ means either group represented by the following formula:

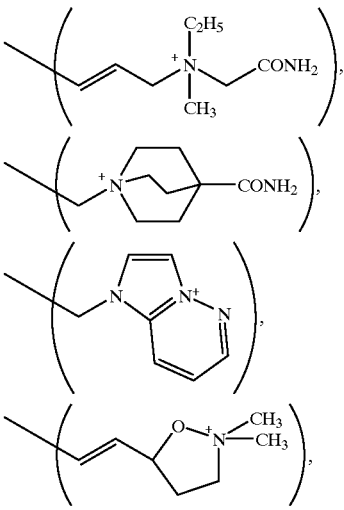

or in which A denotes a nitrogen atom or a methane group, and B is a group selected from among lower alkoxy groups, halogenated lower alkoxy groups, a triphenylmethoxy group, lower alkyl groups, lower acyloxy groups and groups represented by the formula $—C(CH_3)_2COOR$ in which R means a hydrogen atom, an alkali metal atom, an alkaline earth metal atom or an organic cation, with the proviso that A and B may be either a geometric isomer (E) or (Z), $R^2$ denotes a carboxyl group or a carboxyl anion, and $R^3$ stands for a lower alkyl group, a halogen atom, a lower acyloxyalkyl group or any one of groups represented by the following formulae:

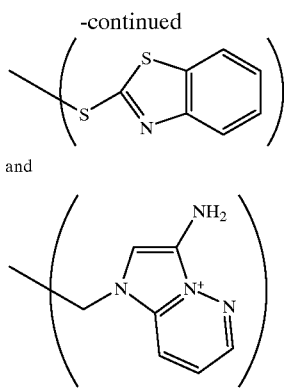
and
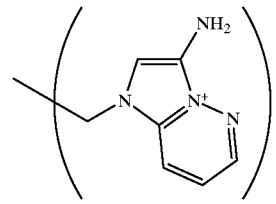

In the present invention, the lower alkoxy groups defined as B in $R^1$ mean linear or branched alkoxy groups having 1–6 carbon atoms. Specific examples thereof may include methoxy, ethoxy, propoxy, butoxy, pentyloxy and hexyloxy groups, with methoxy and isopropoxy groups being preferred.

The halogenated lower alkoxy groups denote the above-described lower alkoxy groups substituted by one or more halogen atoms. Specific examples thereof may include chloromethoxy, fluoromethoxy, dichloromethoxy, difluoromethoxy, trifluoromethoxy, fluoroethoxy and difluoroethoxy groups, with fluoromethoxy and 2-fluoroethoxy group being preferred.

The lower alkyl groups mean linear or branched alkyl groups having 1–6 carbon atoms. Specific examples thereof may include methyl, ethyl, propyl, butyl, pentyl and hexyl groups, with methyl and ethyl being preferred.

The lower acyloxy groups denote linear or branched aliphatic acyloxy groups having 1–6 carbon atoms. Specific examples thereof may include acetoxy, propionyloxy and butyryloxy groups, with an acetoxy group being preferred.

The lower alkyl groups defined in $R^3$ have the same meaning as defined above.

Specific examples of the halogen atoms may include chlorine, bromine, iodine and fluorine atoms, with a chlorine atom being preferred.

The lower acyloxyalkyl groups denote the above-described lower alkyl groups substituted by any of the above-described lower acyloxy groups. Specific examples thereof may include acetoxymethyl, acetoxyethyl, propionyloxymethyl and propionyloxyethyl groups, with an acetoxymethylgroup being preferred.

As the cephem compounds represented by the above formula (III), there have heretofore been known many compounds. More specifically, for example, the following compounds are known to have an excellent pharmacological effect.

(1) 7β-[(Z)-2-(5-Amino-1,2,4-thiadiazol-3-yl)-2-fluoromethoxyiminoacetamide]-3-(E)-(3-carbamoylmethylethyl-methylammonio-1-propenyl)-3-cephem-4-carboxylate,
Generic name: Cefluprenam.

(2) 7β-[(Z)-2-(5-Amino-1,2,4-thiadiazol-3-yl)-2-methoxyiminoacetamide]-3-(4-carbamoylquinuclidinio) methyl-3-cephem-4-carboxylate,
Generic name: Cefclidine.

(3) 7β-[(Z)-2-(5-Amino-1,2,4-thiadiazol-3-yl)-2-methoxyiminoacetamide]-3-(imidazo[1,2-b] pyridazinium-1-yl)-methyl-3-cephem-4-carboxylate,
Generic name: Cefozopran.

(4) 7-(D-αPhenylglycylamino)-3-chloro-3-cephem-4-carboxylic acid,

Generic name: Cefaclor.

(5) 7-(D-α-Phenylglycylamino)-3-methyl-3-cephem-4-carboxylic acid,

Generic name: Cephalexin.

(6) 7-(D-α-Phenylglycylamino)-3-acetoxymethyl-3-cephem-4-carboxylic acid,

Generic name: Cephaloglycin.

(7) 7β-[(Z)-2-(5-Amino-1,2,4-thiadiazol-3-yl)-2-fluoromethoxyiminoacetamide]-3-methyl-3-cephem-4-carboxylic acid.

(8) 7β-[(Z)-2-(5-Amino-1,2,4-thiadiazol-3-yl)-2-fluoromethoxyiminoacetamide]-3-[(E)-2-(2,2-dimethyl-5-isooxazolidinio)vinyl]-3-cephem-4-carboxylic acid, Common name: YM-40220 (34th Interscience Conference on Antimicrobial Agents and Chemotherapy, Paper No. F103)

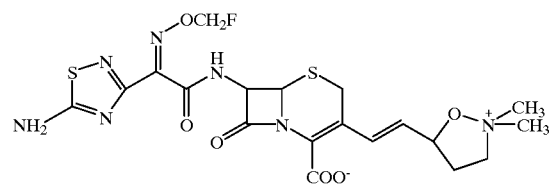

(9) 7β-[(Z)-2-(5-Amino-1,2,4-thiadiazol-3-yl)-2-methoxyiminoacetamide]-3-(benzothiazol-2-yl)thio-3-cephem-4-carboxylic acid, Code name: CP0467

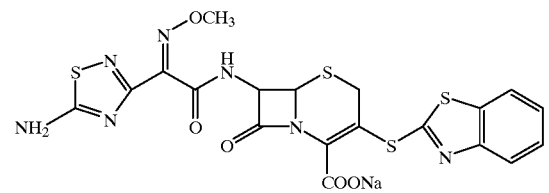

(10) 7β-[(Z)-2-(5-Amino-1,2,4-thiadiazol-3-yl)-2-(1-sodium carboxylate-1-methoxyethoxy)iminoacetamide]-3-(imidazo[1,2-b]pyridazinium-1-yl)methyl-3-cephem-4-carboxylate. (Japanese Patent Application Laid-Open No. 101,960/1995, Example 2)

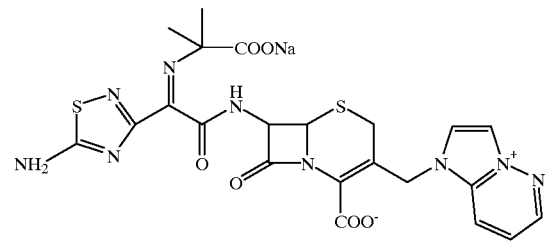

(11) 7β-[(Z)-2-(5-Amino-1,2,4-thiadiazol-3-yl)-2-(2-fluoroethoxyimino)acetamide]-3-(imidazo[1,2-b]-pyridazinium-1-yl)methyl-3-cephem-4-carboxylate. (Japanese Patent Application Laid-Open No. 101,958/1995, Example 1)

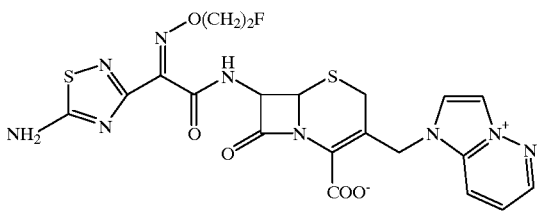

(12) 7β-[(Z)-2-(5-Amino-1,2,4-thiadiazol-3-yl)-2-isopropoxyiminoacetamide]-3-(3-aminoimidazo[1,2-b]-pyridazinium-1-yl)methyl-3-cephem-4-carboxylate. (Japanese Patent Application Laid-Open No. 133,280/1995, Example 2)

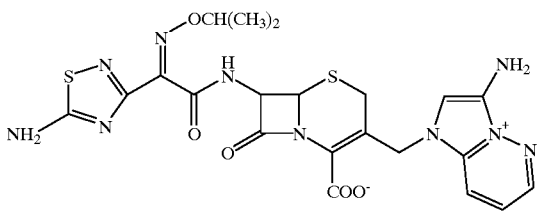

The cephem compounds (III) related to the present invention are not limited to the above-described compounds. However, the present invention exhibits an excellent effect as a production process of the following compounds in particular among others.
(1) 7β-[(Z)-2-(5-Amino-1,2,4-thiadiazol-3-yl)-2-fluoromethoxyiminoacetamide]-3-(E)-(3-carbamoylmethylethyl-methylammonio-1-propenyl)-3-cephem-4-carboxylate,
Generic name: Cefluprenam; and
(2) 7β-[(Z)-2-(5-Amino-1,2,4-thiadiazol-3-yl)-2-methoxyiminoacetamide]3-(4-carbamoylquinuclidinio)methyl-3-cephem-4-carboxylate,
Generic name: Cefclidine.

Incidentally, the cephem compounds (III) related to the present invention may have an asymmetric carbon atom in their molecules. However, the cephem compounds are not limited to particular compounds, and may be either optical isomers, or racemic modifications. Further, they may be hydrates in some cases. No limitation is imposed on the cephem compounds related to the present invention, and the compounds may be anhydrides or n-hydrates [n stands for a real number (an integer or decimal)].

Second, the 3-cephem-4-carboxylate related to the present invention is represented by the following formula (I):

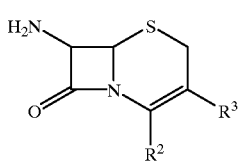

(I)

wherein $R^2$ and $R^3$ have the same meanings as defined above.

More specifically, examples of the 3-cephem-4-carboxylate (I) may include the following compounds to which, however, the invention is not limited. The compounds may be in the form of salts.
(1) 7β-Amino-[(E)-3-carbamoylmethylethylammonio-1-propenyl]-3-cephem-4-carboxylate.
(2) 7β-Amino-3-(4-carbamoylquinuclidinio)methyl-3-cephem-4-carboxylate.
(3) 7β-Amino-3-(imidazo[1,2-b]pyridazinium-1-yl)methyl-3-cephem-4-carboxylate.
(4) 7-Amino-3-chlorocephalosporanic acid.
(5) 7-Amino-3-methylcephalosporanic acid.
(6) 7-Aminocephalosporanic acid.
(7) 7-Amino-3-methylcephalosporanic acid.

The cephem-4-carboxylates (I) related to the present invention are known compounds and generally available in the form of industrial bulk materials or reagents, or the like.

Third, the acid chloride related to the present invention is represented by the formula (II):

$$R^1COCl$$

wherein $R^1$ has the same meaning as defined above.

More specifically, examples of the acid chloride (II) may include the following compounds to which, however, the invention is not limited. The compounds may be in the form of salts.
(1) 2-(5-Amino-1,2,4-thiadiazol-3-yl)-(Z)- 2-fluoromethoxyiminoacetic acid chloride.
(2) (5-Amino-1,2,4-thiadiazol-3-yl)-2-methoxyiminoacetic acid chloride.
(3) Phenylglycine chloride.

The acid chlorides (II) related to the present invention are known compounds and generally available in the form of industrial bulk materials or reagents, or the like.

The present invention is characterized in that the 3-cephem-4-carboxylate (I) or a salt thereof is reacted with the acid chloride (II) in water.

No limitation is imposed on reaction conditions of this reaction. However, the reaction is generally carried out under the following conditions because more preferable effect can be given.
(1) The reaction is performed under conditions of pH 3–7 while adjusting pH by the dropwise addition of a base.
(2) The reaction is performed in the presence of a base in the amount which was previously calculated.

No limitation is imposed on the base in the conditions (1) so far as it is soluble in water and is another base than a primary or secondary amine, and it may be either an inorganic base or an organic base. More specifically, examples of the base may include hydroxides, carbonates, phosphates and tertiary amines. Of these, preferable examples may include sodium hydroxide, potassium hydroxide, aqueous ammonia and triethylamine. Incidentally, these bases may be used either singly or in any combination thereof.

No limitation is also imposed on the pH in the conditions (1) so far as it is within a range of 3–7. However, the pH is generally within a range of preferably 3.5–6.5, more preferably 4–6.

No limitation is also imposed on the reaction temperature so far as it is a temperature, at which the liquid reaction mixture is not frozen, or higher. However, the reaction may be generally carried out at room temperature. At this time, the reaction time varies according to the amount of the solvent used, and the like. However, the reaction is generally completed in about 30 minutes to 6 hours.

No limitation is also imposed on the base in the conditions (2) so far as it is soluble in water and is another base than a primary or secondary amine, and it may be either an inorganic base or an organic base. More specifically, examples of the base may include sodium acetate, potassium acetate, sodium carbonate, potassium carbonate, sodium hydrogencarbonate, potassium hydrogencarbonate, disodium hydrogenphosphate, ammonium carbonate and ammonium carbamate.

No limitation is also imposed on the amount of the base used in the conditions (2). However, the base is used in an amount of generally 1–20 equivalents, preferably 1.5–10 equivalents, more preferably 2–5 equivalents, to the 3-cephem-4-carboxylate (I).

No limitation is also imposed on the reaction temperature so far as it is a temperature, at which the liquid reaction mixture is not frozen, or higher. However, the reaction may be generally carried out at room temperature. At this time, the reaction time varies according to the amount of the solvent used, and the like. However, the reaction is generally completed in about 30 minutes to 6 hours.

No limitation is also imposed on the amount of water which is a solvent used in either of the above-described reactions (1) and (2). However, water is used in an amount of preferably 1–100 ml, more preferably 2–50 ml, most preferably 3–20 ml, per g of the 3-cephem-4-carboxylate (I) from the viewpoint of reaction operability, reaction time or the like.

In the present invention, the liquid reaction mixture per se may be subjected to purification by reverse phase chromatography without replacing water by any other solvent directly after completion of the reaction.

More specifically, after confirming that the reaction has been completed, the liquid reaction mixture can be charged into a reverse phase chromatograph as it is, and subsequently subjected to elution and separation operation. Accordingly, operability is enhanced, and moreover a solvent concentrating step for solvent replacement becomes useless, so that even in a cephem compound unstable to temperature, the risk of forming a thermal decomposition product to reduce yield or find difficulty in purification (reduce purity) can be prevented.

The present invention will hereinafter be described specifically by the following Examples and Comparative Examples. However, it goes without saying that the present invention is not limited to these examples.

EXAMPLE 1

Synthesis of 7β-[(Z)-2-(5-amino-1,2,4-thiadiazol-3-yl)-2-fluoromethoxyiminoacetamide]-3-(E)-(3-carbamoylmethylethylmethylammonio-1-propenyl)-3-cephem-4-carboxylate
(Cefluprenam; E-1077)

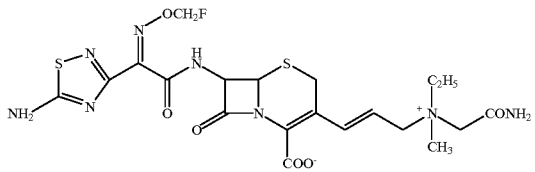

After 12.08 g (30.9 mmol) of 7β-amino-[(E)-3-carbamoylmethylethylammonio-1-propenyl]-3-cephem-4-carboxylate hydrochloride [hereinafter referred to as Compound (1)] were dissolved in 97 ml of water cooled to 9° C., a pH meter was set to add a 5N aqueous solution of NaOH dropwise, thereby adjusting the solution to pH 5. Added to this solution were 8.33 g (30.3 mmol) of 2-(5-amino-1,2,4-thiadiazol-3-yl)-(Z)-2-fluoromethoxyiminoacetic acid chloride-hydrochloride [hereinafter referred to as Compound (2)], and the resultant mixture was stirred for 2 hours while adjusting the mixture with a 5N aqueous solution of NaOH so as to keep it at pH 4.5–5.5. Completion of the reaction was confirmed, and the liquid reaction mixture was purified by reverse phase chromatography (ODS) as it is. Ethanol was added to a main fraction, and the mixture was cooled to −20° C. Crystals deposited were separated, washed with ethanol and then dried to obtain 12.6 g of the title compound. (yield: 73%, HPLC purity: 99.2%).
(Conditions of HPLC analysis)
Stationary phase: ODS (5 μm, 4.6×150 mm)
Mobile phase: 0.5% ammonium acetate/7% aqueous methanol,
flow rate: 1.0 ml/min
Detector: UV 254 nm.
(Physical properties of E-1077)
IR ($cm^{-1}$nujol): 1768, 1689, 1681, 1630, 1602.
$^1$H-NMR (400 MHz, DMSO-$d_6$): δ (ppm) 1.26(3H,t,J=7 Hz), 3.08 & 3.09(3H,s×2), 3.47(1H,d,J=17 Hz), 3.48(2H,m), 3.64(1H,d,J=17 Hz), 4.02(2H,s), 4.13(2H,m), 5.06(1H,d,J=5 Hz), 5.63–5.73(1H,m), 5.64(1H,dd,J=8 Hz,5 Hz), 5.78(2H, d,J=55 Hz), 7.18(1H,d,J=15 Hz), 7.65(1H,s), 8.23(2H,s), 8.37(1H,s), 9.70(1H,d,J=8 Hz).

EXAMPLE 2

Synthesis of 7β-[(Z)-2-(5-amino-1,2,4-thiadiazol-3-yl)-2-fluoromethoxyiminoacetamide]-3-(E)-(3-carbamoylmethylethylmethylammonio-1-propenyl)-3-cephem-4-carboxylate
(Cefluprenam)

After 12.08 g (30.9 mmol) of Compound (1) were dissolved in 97 ml of water cooled to 9° C., a pH meter was set to add a 2N aqueous solution of NaOH dropwise, thereby adjusting the solution to pH 5. Added to this solution were 8.25 g (30.0 mmol) of Compound (2), and the resultant mixture was adjusted with a 2N aqueous solution of NaOH so as to keep it at pH 4.5–5.5. After 2 hours, completion of the reaction was confirmed, the liquid reaction mixture was treated in the same manner as in Example 1 to obtain 12.0 g of the title compound. (yield: 70%).

EXAMPLE 3

Synthesis of 7β-[(Z)-2-(5-amino-1,2,4-thiadiazol-3-yl)-2-fluoromethoxyiminoacetamide]-3-(E)-(3-carbamoylmethylethylmethylammonio-1-propenyl)-3-cephem-4-carboxylate
(Cefluprenam)

After 12.08 g (30.9 mmol) of Compound (1) were dissolved in 97 ml of water cooled to 9° C., a pH meter was set to add a 5N aqueous solution of NaOH dropwise, thereby adjusting the solution to pH 6. Added to this solution were 8.33 g (30.3 mmol) of Compound (2), and the resultant mixture was adjusted with a SN aqueous solution of NaOH so as to keep it at pH 5.5–6.5. After 2 hours, completion of the reaction was confirmed, the liquid reaction mixture was treated in the same manner as in Example 1 to obtain 12.8 g of the title compound. (yield: 74%).

EXAMPLE 4

Synthesis of 7β-[(Z)-2-(5-amino-1,2,4-thiadiazol-3-yl)-2-fluoromethoxyiminoacetamide]-3-(E)-(3-carbamoylmethylethylmethylammonio-1-propenyl)-3-cephem-4-carboxylate
(Cefluprenam)

After 12.08 g (30.9 mmol) of Compound (1) were dissolved in 97 ml of water cooled to 9° C., a pH meter was set to add a 2N aqueous solution of NaOH dropwise, thereby adjusting the solution to pH 6. Added to this solution were 8.33 g (30.3 mmol) of Compound (2), and the resultant mixture was adjusted with a 2N aqueous solution of NaOH so as to keep it at pH 5.5–6.5. After 2 hours, completion of the reaction was confirmed, the liquid reaction mixture was treated in the same manner as in Example 1 to obtain 11.9 g of the title compound. (yield: 69%).

EXAMPLE 5

Synthesis of 7β-[(Z)-2-(5-amino-1,2,4-thiadiazol-3-yl)-2-fluoromethoxyiminoacetamide]-3-(E)-(3-carbamoylmethylethylmethylammonio-1-propenyl)-3-cephem-4-carboxylate (Cefluprenam)

After 12.08 g (30.9 mmol) of Compound (1) were dissolved in 97 ml of water cooled to 9° C., a pH meter was set to add a 2N aqueous solution of NaOH dropwise, thereby adjusting the solution to pH 3. Added to this solution were 9.55 g (34.7 mmol) of Compound (2), and the resultant mixture was adjusted with a 2N aqueous solution of NaOH so as to keep it at pH 2.5–3.5. After 5 hours, completion of the reaction was confirmed, the liquid reaction mixture was treated in the same manner as in Example 1 to obtain 8.2 g of the title compound. (yield: 48%).

EXAMPLE 6

Synthesis of 7β-[(Z)-2-(5-amino-1,2,4-thiadiazol-3-yl)-2-fluoromethoxyiminoacetamide]-3-(E)-(3-carbamoylmethylethylmethylammonio-1-propenyl)-3-cephem-4-carboxylate (Cefluprenam)

After 12.08 g (30.9 mmol) of Compound (1) were dissolved in 120 ml of water cooled to 10° C., a pH meter was set to add a 6.25% aqueous ammonia dropwise, thereby adjusting the solution to pH 5. Added to this solution were 8.07 g (29.3 mmol) of Compound (2), and the resultant mixture was stirred for 2 hours while adjusting the mixture with a 6.25% aqueous ammonia so as to keep it at pH 4.5–5.5. Completion of the reaction was confirmed, and the liquid reaction mixture was treated in the same manner as in Example 1 to obtain 12.4 g of the title compound. (yield: 72%).

EXAMPLE 7

Synthesis of 7β-[(Z)-2-(5-amino-1,2,4-thiadiazol-3-yl)-2-fluoromethoxyiminoacetamide]-3-(E)-(3-carbamoylmethylethylmethylammonio-1-propenyl)-3-cephem-4-carboxylate (Cefluprenam)

After 12.08 g (30.9 mmol) of Compound (1) were dissolved in 120 ml of water cooled to 9° C., a pH meter was set to add a 6.25% aqueous ammonia dropwise, thereby adjusting the solution to pH 6. Added to this solution were 8.07 g (29.3 mmol) of Compound (2), and the resultant mixture was stirred for 2 hours while adjusting the mixture with a 6.25% aqueous ammonia so as to keep it at pH 5.5–6.5. Completion of the reaction was confirmed, and the liquid reaction mixture was treated in the same manner as in Example 1 to obtain 12.2 g of the title compound. (yield: 71%).

EXAMPLE 8

Synthesis of 7β-[(Z)-2-(5-amino-1,2,4-thiadiazol-3-yl)-2-fluoromethoxyiminoacetamide]-3-(E)-(3-carbamoylmethylethylmethylammonio-1-propenyl)-3-cephem-4-carboxylate (Cefluprenam)

After 8.0 g (16.6 mmol) of 7β-amino-[(E)-3-carbamoylmethylethyl methylammonio-1-propenyl]-3-cephem-4-carboxylate hydroiodate were dissolved in 215 ml of water, a pH meter was set to adjust the solution to pH 5 with a 5N aqueous solution of NaOH under cooling with ice water. While keeping the solution at pH 4.5–5.5 under cooling with ice water, 4.0 g (16.8 mmol) of (5-amino-1,2,4-thiadiazol-3-yl)-(Z)-2-fluoromethoxyiminoacetic acid chloride were added to stir the resultant mixture for 2 hours. Completion of the reaction was confirmed, and the liquid reaction mixture was treated in the same manner as in Example 1 to obtain 6.6 g of the title compound. (yield: 71%, HPLC purity: 98.5%).

EXAMPLE 9

Synthesis of 7β-[(Z)-2-(5-amino-1,2,4-thiadiazol-3-yl)-2-fluoromethoxyiminoacetamide]-3-(E)-(3-carbamoylmethylethylmethylammonio-1-propenyl)-3-cephem-4-carboxylate (Cefluprenam)

After 0.78 g (2.0 mmol) of Compound 1 were dissolved in 10 ml of water, 0.56 g (6.6 mmol) of sodium hydrogencarbonate were added. Under cooling with ice water, 0.55 g (2.0 mmol) of Compound (2) were added. After completion of the reaction, the liquid reaction mixture was treated in the same manner as in Example 1 to obtain 0.75 g of the title compound. (yield: 68%).

EXAMPLE 10

Synthesis of 7β-[(Z)-2-(5-amino-1,2,4-thiadiazol-3-yl)-2-fluoromethoxyiminoacetamide]-3-(E)-(3-carbamoylmethylethylmethylammonio-1-propenyl)-3-cephem-4-carboxylate (Cefluprenam)

After 18.22 g (50.9 mmol) of disodium hydrogenphosphate-dodecahydrate were dissolved in 72 ml of water at room temperature, and 5.67 g (14.5 mmol) of Compound (1) were dissolved in this solution, 4.24 g (15.4 mmol) of Compound (2) were added. After completion of the reaction, the liquid reaction mixture was treated in the same manner as in Example 1 to obtain 5.5 g of the title compound. (yield: 68%).

EXAMPLE 11

Synthesis of 7β-[(Z)-2-(5-amino- 1,2,4-thiadiazol-3-yl)-2-fluoromethoxyiminoacetamide]-3-(E)-(3-carbamoylmethylethylmethylammonio-1-propenyl)-3-cephem-4-carboxylate (Cefluprenam)

After 4.17 g (50.9 mmol) of sodium acetate were dissolved in 72 ml of water at room temperature, and 5.67 g (14.5 mmol) of Compound (1) were dissolved in this solution, 4.24 g (15.4 mmol) of Compound (2) were added. After completion of the reaction, the liquid reaction mixture was treated in the same manner as in Example 1 to obtain 5.4 g of the title compound. (yield: 67%).

EXAMPLE 12

Synthesis of 7β-[(Z)-2-(5-amino-1,2,4-thiadiazol-3-yl)-2-fluoromethoxyiminoacetamide]-3-(E)-(3-carbamoylmethylethylmethylammonio-1-propenyl)-3-cephem-4-carboxylate (Cefluprenam)

After 6.33 g (77.2 mmol) of sodium acetate were dissolved in 72 ml of water at room temperature, and 6.01 g (15.4 mmol) of Compound (1) were dissolved in this solution, 4.25 g (15.4 mmol) of Compound (2) were added. After 2 hours, completion of the reaction were confirmed, and the liquid reaction mixture was treated in the same manner as in Example 1 to obtain 5.2 g of the title compound. (yield: 61%).

EXAMPLE 13

Synthesis of 7β-[(Z)-2-(5-amino-1,2,4-thiadiazol-3-yl)-2-methoxyiminoacetamide]-3-(4-carbamoylouinuclidinio)methyl-3-cephem-4-carboxylate (Cefclidine; E-1040)

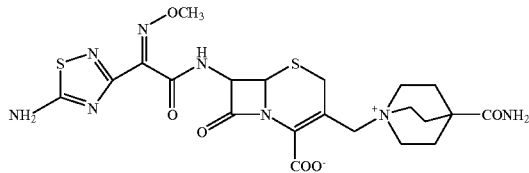

After 7.4 g (20.2 mmol) of 7β-amino-3-(4-carbamoylquinuclidinio)methyl-3-cephem-4-carboxylate [hereinafter referred to as Compound (3)] were dissolved in 180 ml of water, a pH meter was set to adjust the solution to pH 5.5 with a 5N aqueous solution of NaOH under cooling with ice water. While adjusting the resultant mixture to pH 5.0–6.0 with a 5N aqueous solution of NaOH under cooling with ice water, 5.2 g of (5-amino-1,2,4-thiadiazol-3-yl)-(Z)-2-methoxy-iminoacetic acid chloride [hereinafter referred to as Compound (4)] were added, and the resultant mixture was stirred for 1 hour. After completion of the reaction, the liquid reaction mixture was purified by reverse phase chromatography (ODS) as it is. Ethanol was added to a main fraction, and the mixture was allowed to stand-overnight in a refrigerator. Crystals deposited were separated, washed with ethanol and then dried to obtain 7.5 g of the title compound. (yield: 67%, HPLC purity: 98.7%).

(Conditions of HPLC analysis)
Stationary phase: ODS (5 μm, 6.0×150 mm)
Mobile phase: 0.1% ammonium acetate/10% aqueous methanol,
flow rate: 1.5 ml/min
Detector: UV 254 nm.
(Physical properties of E-1040)
Infrared absorption spectrum (cm$^{-1}$, nujol):
3408, 1776, 1672, 1613, 1529, 1392.
$^1$H-NMR (400 MHz, DMSO-d$_6$): δ (ppm) 1.98(6H,3), 3.27(1H,d,J=16.5 Hz), 3.31(3H,m), 3.44(3H,m), 3.75(1H,d,J=16.5 Hz), 3.78(1H,d,J=12.8 Hz), 3.91(3H,s), 4.91(1H,d,J=12.8 Hz), 5.09(1H,d,J=4.8 Hz), 5.67(1H,dd,J=8.4 Hz,4.8 Hz), 7.12(1H,s), 7.29(1H,s), 8.11(2H,s), 9.50(1H,d,J=8.4 Hz).

EXAMPLE 14

Synthesis of 7β-[(Z)-2-(5-amino-1,2,4-thiadiazol-3-yl)-2-methoxyiminoacetamide]-3-(4-carbamoylauinuclidinio)methyl-3-cephem-4-carboxylate (Cefclidine)

After 9.35 g (25.5 mmol) of Compound (3) were dissolved in 250 ml of water, a pH meter was set to adjust the solution to pH 5.5 with a 1N aqueous solution of NaOH under cooling with ice water. Under cooling with ice water, 5.9 g of Compound (4) were added, and the resultant mixture was stirred for 1 hour while adjusting the resultant mixture to pH 5.0–6.0 with a 1N aqueous solution of NaOH. After completion of the reaction, the liquid reaction mixture was treated in the same manner as in Example 13 to obtain 8.6 g of the title compound. (yield: 61%).

REFERENTIAL EXAMPLE 1

Synthesis (conventional process) of 7β-[(Z)-2-(5-amino-1,2,4-thiadiazol-3-yl)-2-methoxyiminoacetamide]-3-(4-carbamoylquinuclidinio)-methyl-3-cepham-4-carboxylate (Cefclidine)

Dissolved in a liquid mixture of 42 ml of water and 126 ml of methanol were 5.2 g of sodium acetate, and 10.5 g of Compound (3) were dissolved in this solution under cooling with ice water. Further, 126 ml of methanol were added, and 7.4 g of Compound (4) were added, followed by continuing stirring for 2 hours. After completion of the reaction, insoluble matter was separated by filtration. Methanol was added dropwise to the filtrate, and the mixture was allowed to stand overnight under cooling ice water. Crystals deposited were separated, washed with methanol, dissolved in water, recrystallized from ethanol, followed by drying to obtain 10.0 g of the title compound. (yield: 63%, HPLC purity: 99.5%).

EXAMPLE 15

Synthesis of 7β-[(Z)-2-(5-amino-1,2,4-thiadiazol-3-yl)-2-methoxyiminoacetamide]-3-(imidazo-[1,2-b]pyridazinium-1-yl)-methyl-3-cephem-4-carboxylate (Cefozopran; SCE-2787)

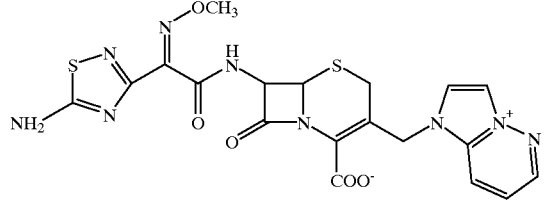

After 14.7 g (40.0 mmol) of 7β-amino-3-(imidazo-[1,2-b]pyridazinium-1-yl)methyl-3-cephem-4-carboxylate [hereinafter referred to as Compound (5)] were dissolved in 220 ml of water under cooling with ice water, 16.4 g (200.0 mmol) of sodium acetate were added. Added to this mixture were 11.3 g (44.1 mmol) of Compound (4). After completion of the reaction, insoluble matter was separated by filtration, and the filtrate was purified by reverse phase chromatography (ODS) as it is. A main fraction was lyophilized to obtain 11.5 g of the title compound. (yield: 56%, HPLC purity: 97.5%).

(Conditions of HPLC analysis)
Stationary phase: ODS (5 μm, 4.6×150 mm)
Mobile phase: 0.1% ammonium acetate/5% aqueous methanol,
flow rate: 1.5 ml/min
Detector: UV 254 nm.
(Physical properties of SCE-2787)
$^1$H-NMR (400 MHz, DMSO-d$_6$): δ (ppm) 3.03 & 3.41 (2H,ABq,J=17.4 Hz), 3.84(3H,s), 4.98(1H,d,J=5.2 Hz), 5.25 & 5.47(2H,ABq,J=14.4 Hz), 5.62(1H,dd,J=4.8 Hz&8.4 Hz), 7.96(1H,dd,J=4.6 Hz&9.4 Hz), 8.13(2H,br-s), 8.77(2H,s), 9.05(1H,dd,J=1.6 Hz,4.4 Hz), 9.34(1H,dd,J=1.2 Hz,9.6 Hz), 9.50(1H,d,J=8.4 Hz).

EXAMPLE 16

Synthesis of 7β-[(Z)-2-(5-amino-1,2,4-thiadiazol-3-yl)-2-methoxyiminoacetamide]-3-(imidazo-[1,2-b]pyridazinium-1-yl)-methyl-3-cephem-4-carboxylate (Cefozopran; SCE-2787)

After 14.7 g (40.0 mmol) of Compound (5) were dissolved in 220 ml of water under cooling with ice water, a pH meter was set to add a 2N aqueous solution of NaOH dropwise, thereby adjusting the solution to pH 5. Added to this solution were 11.3 g (44.1 mmol) of Compound (4). After completion of the reaction, the liquid reaction mixture was treated in the same manner as in Example 15 to obtain 12.5 g of the title compound. (yield: 61%).

EXAMPLE 17

Synthesis of 7β-(D-α-phenylqlycylamino)-3-chloro-3-cephem-4-carboxylic acid
(Cefaclor)

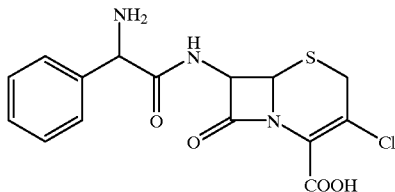

After 2.35 g of 7-amino-3-chlorocephalosporanic acid were dissolved in 80 ml of water, a pH meter was set to adjust the solution to pH 8 with triethylamine under cooling with ice water. While adjusting the solution to pH 4.5–5.5 under cooling with ice water, 2.65 g of (R)-(−)-2-phenylglycine chloride-hydrochloride and triethylamine were alternately added, and the resultant mixture was stirred for 2 hours. After completion of the reaction, the liquid reaction mixture was purified by reverse phase chromatography as it is, and a main fraction was concentrated under reduced pressure. After the concentrated residue was dissolved in 15 ml of 1N HCl, the solution was adjusted to pH 4.5 with triethylamine to crystallize the reaction product. Crystals deposited were separated, washed with ethanol and then dried to obtain 2.58 g of the title compound in the form of a monohydrate. (yield: 66.8%, HPLC purity: 98.0%).
(Conditions of HPLC analysis)
Stationary phase: Inertsil ODS-2 (4.6×150 mm)
Mobile phase: 6% $CH_3CN$/50 mM aqueous solution of $KH_2PO_4$
(pH: 3.4), flow rate: 1.0 ml/min
Detector: UV 254 nm
Internal standard reagent: p-aminoacetophenone.
(Physical properties of Cefaclor)
$^1$H-NMR (400 MHz, $D_2O$/DCl): δ (ppm) 3.1–3.7(ABq, 2H), 5.00(d,1H), 5.57(d,1H), 7.37(s,5H).

EXAMPLE 18

Synthesis of 7β-(D-α-phenylqlycylamino)-3-chloro-3-cephem-4-carboxylic acid
(Cefaclor)

After 14.1 g of 7-amino-3-chlorocephalosporanic acid were dissolved in 960 ml of water, a pH meter was set to adjust the solution to pH 8 with aqueous ammonia under cooling with ice water. While adjusting the solution to pH 4.5–5.5 under cooling with ice water, 17.61 g of (R)-(−)-2-phenylglycine chloride hydrochloride and aqueous ammonia were alternately added, and the resultant mixture was stirred for 2 hours while adjusting it. After completion of the reaction, the liquid reaction mixture was purified by reverse phase chromatography as it is, and a main fraction was concentrated under reduced pressure. After the concentrated residue was dissolved in 150 ml of 1N HCl, the solution was adjusted to pH 4.5 with aqueous ammonia to crystallize the reaction product. Crystals deposited were separated, washed with ethanol and then dried to obtain 16.7 g of the title compound in the form of a monohydrate. (yield: 72.0%, HPLC purity: 98.3%).

EXAMPLE 19

Synthesis of 7β-(D-a-phenylqlycylamino)-3-chloro-3-cephem-4-carboxylic acid
(Cefaclor)

After 14.1 g of 7-amino-3-chlorocephalosporanic acid were dissolved in 960 ml of water, a pH meter was set to adjust the solution to pH 8 with an 8N aqueous solution of NaOH under cooling with ice water. While adjusting the solution to pH 4.5–5.5 under cooling with ice water, 21.83 g of (R)-(−)-2-phenylglycine chloride-hydrochloride and an 8N aqueous solution of NaOH were alternately added, and the resultant mixture was stirred for 2 hours. After completion of the reaction, the liquid reaction mixture was purified by reverse phase chromatography as it is, and a main fraction was concentrated under reduced pressure. After the concentrated residue was dissolved in 150 ml of 1N HCl, the solution was adjusted to pH 4.5 with aqueous ammonia to crystallize the reaction product. Crystals deposited were separated, washed with ethanol and then dried to obtain 13.5 g of the title compound in the form of a monohydrate. (yield: 58.2%, HPLC purity: 97.8%).

EXAMPLE 20

Synthesis of 7β-(D-α-phenylqlycylamino)-3-methyl-3-cephem-4-carboxylic acid
(Cephalexin)

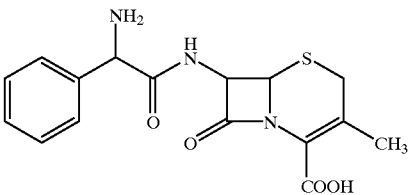

After 3.6 g of 7-amino-3-methylcephalosporanic acid were dissolved in 150 ml of water, and a pH meter was set, the solution was adjusted to pH 8 with aqueous ammonia under cooling with ice water. Under cooling with ice water and stirring, 10.3 g of (R)-(−)-2-phenylglycine chloride were added, and the resultant mixture was stirred for 2 hours while adjusting so as to keep the mixture at pH 8. After completion of the reaction, 1000 ml of acetone were added, and the diluted liquid reaction mixture was allowed to stand-overnight-in a-refrigerator. Crystals deposited were separated, washed with acetone and then dried to obtain 3.8 g of the title compound. (yield: 65%, HPLC purity: 81%).

EXAMPLE 21

Synthesis of 7β-[(Z)-2-(5-amino-1,2,4-thiadiazole-3-yl)-2-fluoromethoxyiminoacetamide]-3-methyl-3-cephem-4-carboxylic acid

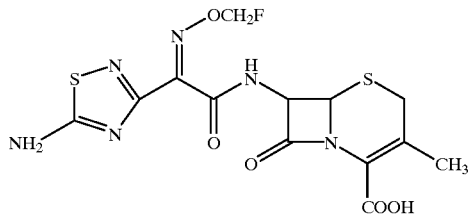

After 3.5 g of 7-amino-3-methylcephalosporanic acid were dissolved in 146 ml of water, a pH meter was set to adjust the solution to pH 8 with aqueous ammonia under cooling with ice water. Under cooling with ice water and stirring, 4.7 g of 2-(5-amino-1,2,4-thiadiazol-3-yl)-(Z)-2-fluoromethoxyiminoacetic acid chloride were added, and the resultant mixture was stirred for 2 hours while adjusting so as to keep the mixture at pH 7.5~8.5. After completion of the reaction, the pH was adjusted to 1–2 with 1N HCl, and the reaction mixture was extracted with 150 ml of ethyl acetate. After the extract was washed with water and dried, it was allowed to stand overnight in a refrigerator. Crystals deposited were separated, washed with ethyl acetate and then dried to obtain 5.1 g of the title compound. (yield: 75%, HPLC purity: 98.3%).

$^1$H-NMR (400 MHz, DMSO-$d_6$): δ (ppm) 2.01(3H,s), 3.33(1H,d,J=19 Hz), 3.57(1H,d,J=19 Hz), 5.10(1H,d,J=5 Hz), 5.74(1H,dd,J=8,5 Hz), 5.79(2H,d,J=55 Hz), 8.19(2H,s), 9.70(1H,d,J=8 Hz), 13.2(1H,br-s).

What is claimed is:

1. A process for producing a cephem compound represented by the following formula (III):

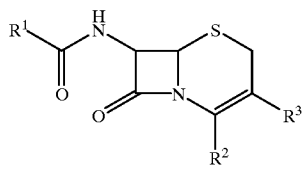

(III)

wherein $R^1$ means either group represented by the following formula:

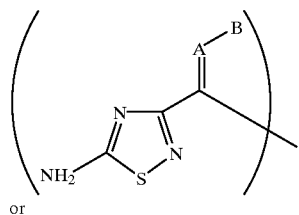

or

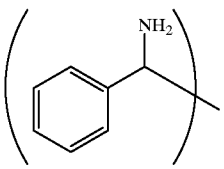

in which A denotes a nitrogen atom or a methine group, and B is a group selected from among lower alkoxy groups, halogenated lower alkoxy groups, a triphenylmethoxy group, lower alkyl groups, alkanoyloxy groups having 1–6 carbon atoms, and groups represented by the formula —C(CH$_3$)$_2$COOR in which R means a hydrogen atom, an alkali metal atom, an alkaline earth metal atom or an organic cation, with the proviso that A and B may be either a geometric isomer (E) or (Z), $R^2$ denotes a carboxyl group or a carboxyl anion, and $R^3$ stands for a lower alkyl group, a halogen atom, a lower alkyl group substituted by an alkanoyloxy group having 1–6 carbon atoms, or any one of the groups represented by the following formulae:

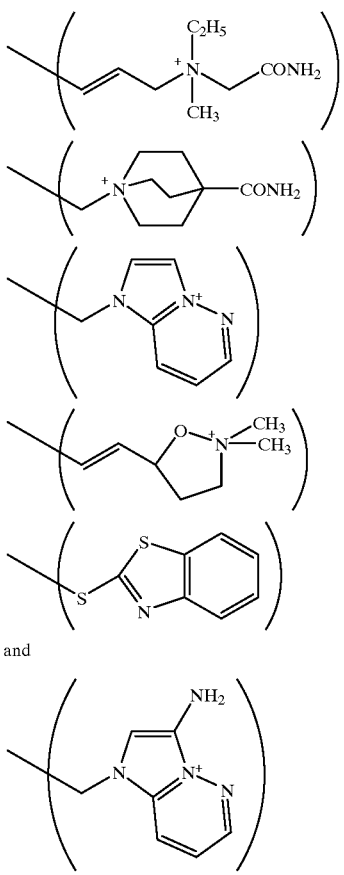

and wherein $R^2$ is a carboxyl anion if and only if the quaternary nitrogen is present, and the quaternary nitrogen is present if and only if $R^2$ is a carboxyl anion, which comprises reacting in water a 3-cephem-4-carboxylate represented by the following formula (I):

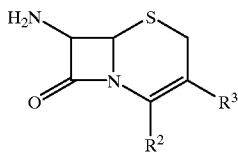

wherein $R^2$ and $R^3$ have the same meanings as defined above, or a salt thereof with an acid chloride represented by the formula (II):

$R^1COCl$ wherein $R^1$ has the same meaning as defined above.

2. The process according to claim 1, wherein the reaction is conducted under conditions of pH 3–7 by adjusting the pH using a base.

3. The process according to claim 2, wherein the base is one or more members selected from the group consisting of sodium hydroxide, potassium hydroxide, aqueous ammonia and triethylamine.

4. The process according to claim 1, wherein the reaction is conducted in the presence of a base.

5. The process according to claim 4, wherein the base is one or more members selected from the group consisting of sodium acetate, potassium acetate, sodium carbonate, potassium carbonate, sodium hydrogencarbonate, potassium hydrogencarbonate, disodium hydrogenphosphate, ammonium carbonate and ammonium carbamate.

6. The process according to claim 1; wherein the cephem compound (III) is 7β-[(Z)-2-(5-amino-1,2,4-thiadiazol-3-yl)-2-fluoromethoxyiminoacetamide]-3-(E)-(3-carbamoylmethylethylmethylammonio-1-propenyl)-3-cephem-4-carboxylate or 7β-[(Z)-2-(5-amino-1,2,4-thiadiazol-3-yl)-2-methoxyiminoacetamide]-3-(4-carbamoylquinuclidinio)-methyl-3-cephem-4-carboxylate.

7. The process according to claim 2, wherein the cephem compound (III) is 7β-[(Z)-2-(5-amino-1,2,4-thiadiazol-3-yl)-2-fluoromethoxyiminoacetamide]-3-(E)-(3-carbamoylmethylethylmethylammonio-1-propenyl)-3-cephem-4-carboxylate or 7β-[(Z)-2-(5-amino-1,2,4-thiadiazol-3-yl)-2-methoxyiminoacetamide]-3-(4-carbamoylquinuclidinio)-methyl-3-cephem-4-carboxylate.

8. The process according to claim 3, wherein the cephem compound (III) is 7β-[(Z)-2-(5-amino-1,2,4-thiadiazol-3-yl)-2-fluoromethoxyiminoacetamide]-3-(E)-(3-carbamoylmethylethylmethylammonio-1-propenyl)-3-cephem-4-carboxylate or 7β-[(Z)-2-(5-amino-1,2,4-thiadiazol-3-yl)-2-methoxyiminoacetamide]-3-(4-carbamoylquinuclidinio)-methyl-3-cephem-4-carboxylate.

9. The process according to claim 4, wherein the cephem compound (III) is 7β-[(Z)-2-(5-amino-1,2,4-thiadiazol-3-yl)-2-fluoromethoxyiminoacetamide]-3-(E)-(3-carbamoylmethylethylmethylammonio-1-propenyl)-3-cephem-4-carboxylate or 7β-[(Z)-2-(5-amino-1,2,4-thiadiazol-3-yl)-2-methoxyiminoacetamide]-3-(4-carbamoylquinuclidinio)-methyl-3-cephem-4-carboxylate.

10. The process according to claim 5, wherein the cephem compound (III) is 7β-[(Z)-2-(5-amino-1,2,4-thiadiazol-3-yl)-2-fluoromethoxyiminoacetamide]-3-(E)-(3-carbamoylmethylethylmethylammonio-1-propenyl)-3-cephem-4-carboxylate or 7β-[(Z)-2-(5-amino-1,2,4-thiadiazol-3-yl)-2-methoxyiminoacetamide]-3-(4-carbamoylquinuclidinio)-methyl-3-cephem-4-carboxylate.

* * * * *